| United States Patent [19] | [11] Patent Number: 4,714,612 |
| --- | --- |
| Nakamura et al. | [45] Date of Patent: Dec. 22, 1987 |

[54] COMPOSITION FOR ORAL APPLICATION

[75] Inventors: Tsuneaki Nakamura, Odawara; Tatsuo Kiyoshige, Hadano; Shuji Sasaki, Hiratsuka, all of Japan

[73] Assignee: Lion Corporation, Tokyo, Japan

[21] Appl. No.: 748,393

[22] Filed: Jun. 24, 1985

[30] Foreign Application Priority Data

Jun. 28, 1984 [JP] Japan ................... 59-132103

[51] Int. Cl.<sup>4</sup> ............................ A61K 39/395
[52] U.S. Cl. ............................ 424/85; 424/101
[58] Field of Search ............... 424/85, 49, 48, 101; 260/112 R, 112 B

[56] References Cited

U.S. PATENT DOCUMENTS

| 4,093,606 | 6/1978 | Coval | 424/107 |
| 4,324,782 | 4/1982 | Beck. | |
| 4,374,763 | 2/1983 | Takagi | 260/112 B |
| 4,442,085 | 6/1982 | Colman et al. | 424/85 |
| 4,454,109 | 6/1984 | Hillman. | |
| 4,458,014 | 7/1984 | Ebersole. | |

FOREIGN PATENT DOCUMENTS

| 981260 | 1/1965 | United Kingdom. |
| 1492383 | 11/1977 | United Kingdom. |
| 1505513 | 3/1978 | United Kingdom. |
| 1545862 | 5/1979 | United Kingdom. |
| 2013691 | 8/1979 | United Kingdom. |
| 1573995 | 3/1980 | United Kingdom. |

OTHER PUBLICATIONS

Mouton et al., Infect, Immun., 31 (1), pp. 182–192 (1981).

Primary Examiner—Blondel Hazel
Attorney, Agent, or Firm—Birch, Stewart, Kolasch & Birch

[57] ABSTRACT

A composition for oral application comprises a nonspecific γ-globulin as an effective ingredient for preventing Bacteroides gingivalis from colonizing in the mouth.

8 Claims, No Drawings

COMPOSITION FOR ORAL APPLICATION

BACKGROUND OF THE INVENTION

The present invention relates to a composition for oral application to prevent and remedy the periodontal diseases such as gingivitis, and more particularly, it relates to a composition for oral application to prevent Bacteroides gingivalis, which is one of the bacteria that cause periodontal diseases, from colonizing in the mouth and thereby to prevent periodontal diseases.

There are many people having periodontal disease such as gingivitis and periodontitis. The rate of such disease in adults is especially on the increase. Prevention of periodontal diseases will be an important problem under the future circumstance of an ever more increasing number of aged persons.

Periodontal disease is primarily caused by bacteria existing in accumulated plaque in periodontal pockets. A healthy periodontal pocket is usually composed of an overwhelming amount of gram positive bacteria, while the amount of gram negative bacteria increases with the progress of the periodontal disease. *Bacteroides gingivalis, Fusobacterium nucleatum, Eikenella corrodens, Actinobacillus actinomycetemcomitans* and so forth are primarily listed as such gram negative bacteria. In the focal regions of adult patients with severe periodontal disease, gram negative bacteria are detected in most cases among which Bacteroides gingivalis is separated in a specially high frequency. In many of these cases, the titer of anti-Bacteroides gingivalis antibody in the serum of the patient also increases. In addition, it has been demonstrated that the inoculation of an animal with Bacteroides gingivalis aggravates periodontal inflammation. These results indicate that Bacteroides gingivalis plays an important role in the development of periodontal diseases.

Bacteroides gingivalis adheres to periodontal mucosa by means of its pili and capsule existing on the surface of its bacterial body, thereby proliferating and badly influencing the periodontal region. For the prevention of periodontal diseases, the inhibition of the colonization or suppression of the proliferation of Bacteroides gingivalis in the mouth is effective and bactericides are mainly used now to prevent periodontal disease. The use of a bactericide, however, is not desirable because it indiscriminately kills bacteria in the mouth and changes the bacterial flora in the mouth. In some more specific methods, the inhibition of the colonization of Bacteroides gingivalis in the mouth is attempted by using a vaccine. However, since the whole bacterial cell is used as an active vaccine directly injected into the living human body in all of these methods, they have problems in terms of both effect and toxicity.

SUMMARY OF THE INVENTION

An object of the present invention is to provide a composition for oral application having an excellent effect on preventing periodontal disease.

For the purpose of attaining the above object, the present inventors conducted on a highly safe method of securing the prevention of periodontal disease through effective suppression of the colonization of the causative bacteria of periodontal disease, especially Bacteroides gingivalis in the mouth. As a result, the inventors have found that the oral administration of nonspecific γ-globulin is effective.

γ-Globulin preparations have been known as being effective in preventing and curing measles, asthma, varicella, and polio, and they are used in the form of intramuscular injections. However, it has not been known that γ-globulin is effective against periodontal diseases. Unexpectedly, the investigation by the present inventors revealed that nonspecific γ-globulin prevents Bacteroides gingivalis from colonizing in the mouth when it is intraorally administered, and that periodontal diseases can be effectively prevented by blending nonspecific γ-globulin in a composition for oral application.

Therefore, the present invention provides a composition for oral application comprising a nonspecific γ-globulin as an effective ingredient for suppressing the intraoral colonization of Bacteroides gingivalis According to this invention, since the composition contains the nonspecific γ-globulin, the colonization of Bacteroides gingivalis in the mouth is effectively prevented, resulting in the prevention of periodontal disease such as periodontitis.

In addition, since the nonspecific γ-globulin is highly safe, the composition according to this invention can be safely used.

The above and other objects, features, and advantages of this invention will be more fully understood by reading the following description.

DETAILED DESCRIPTION OF THE INVENTION

The composition for oral application of the present invention contains a nonspecific γ-globulin, and may be prepared and used in various forms applicable to the mouth such as dentifrices including toothpastes, toothpowders and liquid dentifrices, liquid refrigerants including mouthwashes, solid refrigerants including troches and chewing gums, dental pastes, gingival massage creams, gargle tablets, dairy products including ice creams, yogurts and babaroa bases, injections and the like. It may be applied to the gingiva and other affected parts in the mouth by various methods including brushing, gargling, massaging applying, chewing and injecting. The scope of this invention covers those compositions which are applied to the mouth of mammals such as horses, cattle, goats, pigs, dogs, cats, and to the mouth of poultry.

According to this invention, the composition for oral application is incorporated with nonspecific γ- globulin as an effective ingredient for the prevention and remedy of periodontal disease. In the case where the composition is to be applied to a human, human γ-globulin may preferably be used, and the one for mammals may preferably contain γ-globulin derived from the same species of animal to which it is applied. In addition, since γ-globulin is as safe as proteins in the feed, γ-globulin derived from the different species of animal to which it is applied may also be used preferably. The nonspecific γ-globulin may be prepared by the well-known methods. For example, it can be prepared from blood by the steps of separating serum, performing salting-out with ammonium sulfate solution and performing dialysis with water. It also can be prepared from milk by the steps of centrifuging to collect the intermediate layer, performing salting-out with ammonium sulfate solution and performing dialysis with water. Commercially available γ-globulins can also be used.

The amount of γ-globulin (dry basis) to be incorporated in the composition varies depending on the kind of the composition. In most cases, it is 0.001 to 10% by weight, particularly 0.01 to 1% by weight of the composition, so that the dose of γ-globulin is 0.01 to 100 mg, preferably 0.05 to 50 mg, per kg per day. In the case of injections, the preferred dose is 10 to 300 mg, particularly 25 to 100 mg, per kg per day.

The composition according to this invention may further include additional well-known ingredients depending on the type and form of a particular composition. Any desired known ingredients may be mixed with the nonspecific γ-globulin.

In preparing dentifrice compositions, an abrasive may be blended generally in an amount of 5 to 95%, especially 15 to 60% by weight of the composition, including dicalcium phosphate dihydrate, dicalcium phosphate anhydrate, monocalcium phosphate, tricalcium tertiary phosphate, calcium carbonate, calcium pyrophosphate, silica abrasives, aluminosilicate, aluminum oxide, aluminum hydroxide, insoluble sodium metaphosphate, trimagnesium phosphate, magnesium carbonate, calcium sulfate, titanium dioxide, resins, and the like.

In preparing paste-like compositions, typically toothpastes, a binder may be blended generally in an amount of 0.3 to 5% by weight, including sodium carboxymethyl cellulose, methyl cellulose, sodium carboxymethyl hydroxyethyl cellulose, hydroxyethyl cellulose, sodium alginate, carrageenan, gum arabic, tragacanth gum, karaya gum, polyvinylalcohol, sodium polyacrylate, carboxyvinyl polymer, polyvinyl pyrrolidone, and the like.

In preparing paste-like and liquid oral compositions, typically toothpastes and mouthwashes, a humectant may be blended generally in an amount of 10 to 70% by weight, including polyethylene glycol, ethylene glycol, sorbitol, glycerol, propylene glycol, 1,3-butylene glycol, xylitol, maltitol, lactitol, and the like.

In addition to the above ingredients, a surface active agent including water soluble salts of alkyl sulfate having 8 to 18 carbon atoms such as sodium laurate and sodium myristate, sodium salts of higher fatty acids, water-soluble salts of sulfonates monoglycerides of higher fatty acids having 10 to 18 carbon atoms in the fatty acid group such as sodium lauryl monoglyceride sulfonate and sodium coconut monoglyceride sulfonate, sodium monoglyceride monosulfates of higher fatty acids, olefin sulfonates, paraffin sulfonates, sodium N-methyl-N-palmitoyl taurate, sodium N-lauroyl sarcosinate, sodium N-lauroyl-β-alaninate, stearyl monoglyceride, alkyrol ethanol amides such as lauroyl monoethanol amide and lauroyl diethanol amide, sucrose fatty acid esters having 12 to 18 carbon atoms in the fatty acid group such as sucrose monolaurate and dilaurate, lactose fatty acid esters, lactitol fatty acid esters, maltitol fatty acid esters, stearic acid monoglyceride, polyoxyethylene sorbitan monolaurate, polyoxyethylene-hardened castor oil, condensates of sorbitan monostearate with approximately 60 moles of ethylene glycol, condensates of ethylene oxide with propylene oxide, and their derivatives such as polyoxyethylene polyoxypropylene monolauryl ester, betaine and amino acid type amphoteric surfactants, and the like may be blended in an amount of 0 to 10%, preferably 0.1 to 5%, more preferably 1 to 2.5% by weight of the composition. A flavor such as an essential oil including peppermint oil and spearmint oil and a flavoring material including l-menthol, carvone, eugenol and anethole, a sweetener such as sodium saccharinate, stevioside, neohesperidyldihydrochalcone, glycyrrhizin, perillartine, p-methoxycinnamic aldehyde, a preservative, and the like may be blended in an effective amount.

In this invention, effective ingredients such as sorbic acid, alexidine, hinokitiol, cetylpyridinium chloride, alkyl glycine, alkyldiaminoethyl glycinate, allantoin, ε-aminocaproic acid, tranexamic acid, azulene, vitamin E, a water soluble primary or secondary phosphate, a quaternary ammonium compound, sodium chloride, enzymes such as dextranase, mutanase, lytic enzyme and protease, fluoride compounds such as sodium fluoride, stannous fluoride and sodium monofluorophosphate, chlorhexidine and its salts, bacteriocin, glucosyltransferase inhibitor, and crude drugs and their extracts may also be blended in an effective amount.

Other types of compositions may also be prepared by selecting any desired ingredients as usual and mixing them by a conventional procedure.

Examples of the other ingredients for various types or forms of the composition are shown in the following examples.

Paste-like and liquid oral compositions may generally have a pH ranging from 5 to 10, but not limited thereto.

The composition for oral application of this invention may be formulated into liquid that can be used for injections or powder that can be prepared into injections upon application. The composition in the form of injections may be incorporated with a proper stabilizer (e.g., aminoacetic acid), preservative (e.g., thimerosal), and tonicity agent (e.g., sodium chloride) in the usual way.

The composition of this invention may be applied in the known manner according to the respective formulations. Preferably it should be applied so that it acts on oral bacteria, and good effects are resulted when it is applied to the inflamed gingiva for periodontal disease. The composition in the form of injections may be injected into the gingiva.

On account of nonspecific γ-globulin incorporated therein as mentioned above, the composition for oral application of this invention prevents Bacteroides gingivalis from colonizing in the mouth and thereby effectively prevents and remedies the periodontosis such as gingivitis and periodentitis.

The invention is now described in more detail with reference to the following examples, in which "%" means "% by weight" and the quantity of γ-globulin is expressed on dry basis.

EXAMPLE 1

(1) Preparation of γ-globulin:

γ-Globulin from blood

γ-Globulin was prepared from blood of healthy rabbits by the steps of separating serum, performing salting-out twice with 50% ammonium sulfate solution, and performing dialysis with distilled water according to a known method.

γ-Globulin was prepared from goat milk by the steps of centrifuging at 1500 rpm for 1 hour to collect the intermediate layer, performing salting-out twice with 50% ammonium sulfate solution, and performing dialysis with distilled water according to a known method.

(2) Effect of rabbit γ-globulin on preventing Bacteroides gingivalis from colonizing in the hamster mouth.

Sixteen male golden hamsters arranged in test group and control group, each group consisting of eight hamsters, were grown with powder feed and free watering (tap water) until they were slaughtered. On the first day, the hamsters in both groups were treated as follows: The first molars on both sides of the lower jaw were tied with a cotton thread (No. 50). Each molar was inoculated with Bacteroides gingivalis 381-R' by dropping 0.1 ml of suspension containing $1 \times 10^8$ living bacteria per ml. Thirty minutes later, the hamsters in test group were administered with a 50:50 mixture of nonspecific rabbit $\gamma$-globulin and glycerin at a dose of 0.05 ml for each molar, and then the rows of molars (both the under side and the buccal side) were brushed 20 times in the presence of the mixture. For the control group, on the other hand, brushing was performed in the same way as mentioned above using a 50:50 mixture of distilled water and glycerin. The above procedure was repeated during three consecutive days, and on the fourth day and subsequent days, brushing alone was performed twice a day.

The cottom thread used for tying was recovered one week and three weeks after the inoculation of living bateria, and the number of Bateroides gingivalis and the total number of anaerobic bacteria in the cotton thred were counted. Table 1 shows the number of hamsters in which Bacteroides gingivalis colonized and the ratio of colonization which is represented in percentage of the number of Bacteroides gingivalis in the total number of anaeobic bacteria.

TABLE 1

| | Number of colonization | Ratio of colonization |
|---|---|---|
| After one week | | |
| Test group | 8/8 | 0.53 ± 0.20% |
| Control group | 8/8 | 1.07 ± 0.48% |
| After three weeks | | |
| Test group | 5/8 | 0.025 ± 0.041% |
| Control group | 7/8 | 0.951 ± 0.493% |

Remarks:
"Number of colonization" is the number of hamsters in which *Bacteroides gingivalis* colonized divided by the total number of hamsters tested.
"Ratio of colonization" is the number of *Bacteroides gingivalis* divided by the total number of anaerobic bacteria multiplied by 100 plus or minus SD.

It is to be noted in Table 1 that colonization of Bacteroides gingivalis was observed in five cases out of eight in the test group three weeks after inoculation, and this is smaller than that in the control group. In addition, the ratio of colonization was apparently low in the test group when measured three weeks after inculation. This indicates that the topical administration of $\gamma$-globulin prevents Bacteroides gingivalis from colonizing and is effective against periodontal diseases.

EXAMPLE 2 (Toothpaste)

| | |
|---|---|
| Dicalcium phosphate dihydrate | 50.0% |
| Glycerin | 20.0 |
| Sodium carboxymethylcellulose | 1.0 |
| Sodium lauryl sulfate | 1.5 |
| Sodium lauroyl sarcosinate | 0.5 |
| Flavor | 1.0 |
| Sodium saccharin | 0.1 |
| Dextranase | 0.01 |
| Water | Balance |
| Total | 100.0% |

In addition to the above ingredients, the toothpaste was incorporated with 0.01% or 0.05% of human $\gamma$-globulin and 0.01% of chlorhexidine gluconate.

EXAMPLE 3 (Toothpaste)

| | |
|---|---|
| Dicalcium phosphate dihydrate | 50.0% |
| Sorbitol | 10.0 |
| Glycerin | 10.0 |
| Sodium carboxymethylcellulose | 1.0 |
| Sodium lauryl sulfate | 2.0 |
| Flavor | 1.0 |
| Sodium saccharin | 0.1 |
| Ethanol | 2.0 |
| Mutanase | 0.1 |
| Water | Balance |
| Total | 100.0% |

In addition to the above ingredients, the toothpaste was incorporated with 0.01% or 0.05% of human $\gamma$-globulin, and 0.3% of sodium monofluorophosphate or 0.01% of chlorhexidine gluconate or 0.05% of lytic enzyme or 0.02% of bacteriocin.

EXAMPLE 4 (Toothpaste)

| | |
|---|---|
| Calcium carbonate | 50.0% |
| Glycerin | 20.0 |
| Carrageenan | 0.5 |
| Sodium carboxymethylcellulose | 1.0% |
| Lauroyl djethanolamide | 1.0 |
| Sucrose monolaurate | 2.0 |
| Flavor | 1.0 |
| Sodium saccharin | 0.1 |
| Water | Balance |
| Total | 100.0% |

In addition to the above ingredients, the toothpaste was incorparated with 0.05% of human $\gamma$-globulin, 0.005% of chlorhexidine gluconate, and 0.05% of tranexamic acid.

EXAMPLE 5 (Toothpaste)

| | |
|---|---|
| Dicalcium phosphate dihydrate | 50.0% |
| Glycerin | 20.0 |
| Sodium carboxymethylcellulose | 2.0 |
| Sodium lauryl sulfate | 2.0 |
| Flavor | 1.0 |
| Sodium saccharin | 0.1 |
| Water | Balance |
| Total | 100.0% |

In addition to the above ingredients, the toothpaste was incorporated with 0.01% of horse $\gamma$-globulin.

EXAMPLE 6 (Paste Toothpaste)

| | |
|---|---|
| Silicic anhydride | 30.0% |
| Glycerin | 30.0 |
| Sorbitol | 20.0% |
| Sodium carboxymethylcellulose | 1.0 |
| Sodium lauryl sulfate | 2.0 |
| Flavor | 1.0 |
| Sodium saccharin | 0.1 |
| Ethanol | 2.0 |
| Water | Balance |
| Total | 100.0% |

In addition to the above ingredients, the toothpaste was incorporated with 0.02% of cattle $\gamma$-globulin, and 0.1% of sodium fluoride or 0.01% of chlorhexidine gluconate or 0.1% of lytic enzyme or 0.01% of bacteriocin.

EXAMPLE 7 (Toothpaste)

| | |
|---|---|
| Dicalcium phosphate dihydrate | 50.0% |
| Calcium carbonate | 30.0 |
| Glycerin | 10.0 |
| α-Olefin sulfonate | 1.0 |
| Flavor | 1.0 |
| Sodium saccharin | 0.1 |
| Dextran | 0.5 |
| Water | Balance |
| Total | 100.0% |

In addition to the above ingredients, the toothpowder was incorporated with 0.03% of human γ-globulin, and 0.01% of chlorhexidine gluconate or 0.05% of lytic enzyme or 0.001% of bacteriocin.

EXAMPLE 8 (Liquid dentifrice)

| | |
|---|---|
| Sodium polyacrylate | 50.0% |
| Glycerin | 30.0 |
| Flavor | 0.9 |
| Sodium saccharin | 3.0 |
| Linolic acid | 0.05 |
| Water | Balance |
| Total | 100.0% |

In addition to the above ingredients, the liquid dentifrice was incorporated with 0.01% of human γ-globuloin, 0.05% of chlorhexdine gluconate, and 0.05% of lytic enzyme or 0.001% of bacteriocin.

EXAMPLE 9 (Mouthwash)

| | |
|---|---|
| Ethanol | 20.0% |
| Flavor | 1.0 |
| Sodium saccharin | 0.05 |
| Lauroyl diethanolamide | 0.3 |
| Water | Balance |
| Total | 100.0% |

In addition to the above ingredients, the mouthwash was incorporated with 0.05% of human γ-globulin and 0.01% of chlorhexidine gluconate.

EXAMPLE 10 (Gargle tablet)

| | |
|---|---|
| Sodium hydrogen carbonate | 54.0 parts by weight |
| Sodium secondary phosphate | 10.0 parts by weight |
| Polyethylene glycol | 3.0 parts by weight |
| Citric acid | 17.0 parts by weight |
| Sodium sulfate (anhydrous) | 13.6 parts by weight |
| Flavor | 2.0 parts by weight |
| Oleic acid | 0.1 parts by weight |

In additon to the above ingredients, the gargle tablet was incorporated with 0.01% of human γ-globulin and 0.05% of chlorhexidine gluconate or 0.05% of lytic enzyme or 0.01% of bacteriocin.

EXAMPLE 11 (Gingiva massage cream)

| | |
|---|---|
| White vaselin | 8.0% |
| Propylene glycol | 4.0 |
| Stearyl alcohol | 8.0 |
| Polyethylene glycol 4000 | 25.0 |
| Polyethylene glycol 400 | 37.0 |
| Sucrose stearate | 0.5 |
| Water | Balance |
| Total | 100.0% |

In addition to the above ingredients, the cream was incorporated with 0.05% of human γ-globulin and 0.01% of chlorhexidine gluconate or 0.1% of tocopherol acetate.

EXAMPLE 12 (Chewing gum)

| | |
|---|---|
| Gum base | 44.0% |
| Calcium carbonate | 2.0 |
| Corn syrup | 15.0 |
| Sugar | 30.0 |
| Sucrose palmitate | 1.0 |
| Fructose | 4.0 |
| Maltose | 3.0 |
| Flavor | 1.0 |
| Total | 100.0% |

In addition to the above ingredients, the chewing gum was incorporated with 0.01% of human γ-globulin and 0.01% of chlorhexidine gluconate or 0.1% of lytic enzyme or 0.01% of bacteriocin.

EXAMPLE 13 (Troche)

| | |
|---|---|
| Gum arabic | 6.0% |
| Glucose | 72.0 |
| Gelatin | 3.0 |
| Flavor | 0.2 |
| l-Menthol | 0.1 |
| Spearmint oil | 0.1 |
| Sodium ascorbate | 0.1 |
| Water | Balance |
| Total | 100.0% |

In addition to the above ingredinets, the troche was incorporated with 0.001% of human γ-globulin and 0.01% of chlorhexidine gluconate or 0.05% of lytic enzyme or 0.01% of bacteriocin or 0.05% of tocopherol nicotinate.

EXAMPLE 14 (Buccal paste)

| | |
|---|---|
| Polyoxyethylene monostearate | 2.0% |
| Sorbitan monooleate | 2.0 |
| Myristyl alcohol | 2.0 |
| Palmityl alcohol | 3.0 |
| Propylene glycol | 15.0 |
| Sodium carboxymethylcellulose | 5.0 |
| Gelatin | 1.0 |
| Sodium saccharin | 0.2 |
| Peppermint oil | 0.5 |
| Spearmint oil | 0.5 |
| Lysozyme chloride | 5000 units/g |
| Water | Balance |
| Total | 100.0% |

In additon to the above ingredients, the paste was incorporated with 0.001% or 0.05% of human γ-globulin and 0.1% of stannous fluoride or 0.01% of chlorhexidine hydrochloride or 0.05% of lytic enzyme or 0.01% of bacteriocin.

EXAMPLE 15 (Buccal paste)

| | |
|---|---|
| Glyceryl monostearate | 3.0% |
| Oleyl alcohol | 5.0 |
| Polyethylene glycol | 15.0 |

| -continued | |
|---|---|
| White vaselin | 3.0 |
| Monosodium N—palmitoylglutamate | 0.5 |
| Hydroxyethylcellulose | 5.0 |
| Tocopherol acetate | 0.1 |
| Sodium saccharin | 0.2 |
| Mentha oil | 0.7 |
| Carvone | 0.5 |
| Anethole | 0.3 |
| Eugenol | 0.1 |
| Water | Balance |
| Total | 100.0% |

In addition to the above ingredients, the paste was incorporated with 0.05% of human γ-globulin, 0.01% of chlorhexidine hydrochloride, and 0.1% of β-glycyrrhetinic acid.

EXAMPLE 16 (Ice cream)

| Cream (fat 50%) | 16.84% |
|---|---|
| Cow's milk (fat 3.7%) | 42.67 |
| Evaporated condensed skim milk | 24.24 |
| Sugar | 11.25 |
| Corn syrup | 4.65% |
| Stabilizer | 0.35 |
| Total | 100.0% |

In addition to the above ingredients, the ice cream was incorporated with 0.1% of cattle γ-globulin.

EXAMPLE 17 (Ice cream)

| Cream (fat 40%) | 31.54% |
|---|---|
| Cow's milk (fat 3.7%) | 37.16 |
| Evaporated condensed skim milk | 15.08 |
| Sugar | 11.25 |
| Corn syrup | 4.67 |
| Stabilizer | 0.30 |
| Total | 100.0% |

In addition to the above ingredients, the ice cream was incorporated with 0.5% of cattle γ-globulin.

EXAMPLE 18 (Yoghurt)

| Skim milk | 320 kg |
|---|---|
| Sweetened condensed milk | 56 |
| Sugar | 23 |

Yoghurt was produced by fermentation in the usual way.

EXAMPLE 19 (Bavaroise dough)

| Cow's milk | 370 cc |
|---|---|
| Sugar | 60 g |
| Vanilla sheath | 1 piece |
| Egg yolk | 5 pieces |
| Gelatin | 20 g |
| Raw cream | 75 cc |

In addition to the above ingredients of Examples 18 and 19, 0.5% of cattle γ-globulin were incorporated.

EXAMPLE 20

Wister male rats arranged in test group and control group, each consisting of 10 rats, were grown with Keyes diet 2000 for 12 weeks (112 age in day) from weaning (at 28 age in day) to slaughter. The rats in test group were given twice each of γ-globulin in (made by Miles Laboratories, Inc. and Cappel Laboratories, Inc.) by injection into the tail vein at 84 age in day (12 age in week) and 109 age in day (3 days before slaughter). The rats in control group were given twice 1 ml each of sterillized phosphate buffer solution on the same age in day as above.

Immediately after injection of γ-globulin in or phosphate buffer solution and immediately before slaughter, blood was collected from the tail vein or orbit. After standing at 4° C. for 30 minutes, the blood was centrifuged at 2500 rpm for 10 minutes to separate serum. The serum was stored at −70° C.

Immediately after slaughter with ether, the upper and lower jaws were washed with physiological saline solution and fixed with 10% formalin. After deliming with Plank-Rychlo deliming solution, block sections were prepared for mesiodistal sectional specimens.

The specimen was embedded in paraffin according to Heeley method and 8-μm thick sections were prepared, followed by dyeing with hematoxylin-eosin double stain. For each rat, four sections of the upper jaw and four sections of lower jaw were examined for the number of polymorphonuclear and mononuclear infiltration cells at each mamillary body. By using eight specimens for each rat, the ratio of the infiltration region to the mamillary body connective tissue in the area from the cement-enamel boundary to the tooth crown was measured with a planimeter according to Line method. The results are shown in Table 2.

TABLE 2

| | Rat No. | Number of infiltration cells | Infiltration area (%) |
|---|---|---|---|
| Test group | 1 | 177 | 24.0 |
| | 2 | 321 | 38.5 |
| | 3 | 65 | 22.5 |
| | 4 | 219 | 18.5 |
| | 5 | 148 | 26.8 |
| | 6 | 228 | 34.3 |
| | 7 | 500 | 38.0 |
| | 8 | 181 | 14.3 |
| | 9 | 273 | 17.0 |
| | 10 | 374 | 20.8 |
| | Average | 249 ± 39 | 25.5 ± 2.8 |
| Control group | 11 | 175 | 19.8 |
| | 12 | 298 | 19.0 |
| | 13 | 154 | 31.3 |
| | 14 | 159 | 25.0 |
| | 15 | 159 | 58.0 |
| | 16 | 345 | 35.3 |
| | 17 | 451 | 24.0 |
| | 18 | 344 | 34.2 |
| | 19 | 446 | 31.3 |
| | 20 | 271 | 38.3 |
| | Average | 280 ± 37 | 31.6 ± 3.6 |

It is to be noted from Table 2 that the number of infiltration cells and the infiltration area are lower in test group (which was given γ-globulin) than in control group. This result suggests that γ-globulin is effective against periodontal diseases.

It is known that the cellular infiltration of leukocytes and the decomposition of connective tissue components take place in the early stage of periodontal diseases, and the disintegration of connective tissues and the extreme infiltration of plasma cells take place in the matured stage. This suggests that suppressing the infiltration of cell is effective against periodontal diseases. It was observed in this example that the infiltration of gingival cells is effectively suppressed by injection of γ-globulin.

EXAMPLE 21

An injection of the following formula was prepared.

| | |
|---|---|
| Human γ-globulin | 15% |
| Aminoacetic acid | 2.25% |
| Methylol | 0.01% |
| Distilled water for injection | Balance |
| Total | 100.0% |
| pH | 6.4 to 7.2 |

For the prevention and remedy of human marginal periodontosis of patient at $P_1$ and $P_2$ levels, this injection is injected into the inflamed root of a tooth at a dose of 50 mg of γ-globulin (equivalent to 0.33 ml of the injection) per kg of body weight after scaling in order to alleviate inflammation and to prevent the resorption of the alvolar bone. For patients at $P_3$ level, it is injected in the same manner after scaling at a dose of 75 mg of γ-globulin (equivalent to 0.50 ml of the injection) per kg of body weight.

For the prevention and remedy of dog's and cat's periodontosis, an injection of the same formula as above (except the type of γ-globulin is different) is injected into the inflamed root of a tooth at a dose of 25 mg of γ-globulin per kg of body weight. In either cases, good results were obtained.

What is claimed is:

1. A method for preventing Bacteroides gingivalis from colonizing in the mouth comprising intraorally administering an effective amount of a non-specific γ-globulin to prevent Bacteroides gingivalis from colonizing in the mouth.

2. The method as set forth in claim 1, wherein the nonspecific γ-globulin is one which is derived from a mammal.

3. The method as set forth in claim 1, wherein the nonspecific γ-globulin is human γ-globulin.

4. The method as set forth in claim 1, wherein the method of administering is selected from the group consisting of brushing, gargling, massaging, and chewing.

5. The method as set forth in claim 1, wherein the non-specific γ-globulin is applied to the mouth of mammals selected from the group consisting of humans, horses, cattle, goats, pigs, dogs and cats.

6. The method as set forth in claim 1, wherein the dose of γ-globulin is 0.001 to 100 mg per kg per day.

7. The method as set forth in claim 1, wherein the dose of γ-globulin is 0.05 to 50 mg per kg per day.

8. The method as set forth in claim 1, wherein the composition is applied to inflamed gingiva.

* * * * *